United States Patent [19]

Beall et al.

[11] 4,347,222
[45] Aug. 31, 1982

[54] GAS GENERATING APPARATUS FOR ANAEROBIC ATMOSPHERE

[75] Inventors: Glenn L. Beall, Gurnee; Robert P. Noonan, Naperville, both of Ill.

[73] Assignee: Miles Laboratories, Inc., Elkhart, Ind.

[21] Appl. No.: 257,512

[22] Filed: Apr. 21, 1981

[51] Int. Cl.³ .............................................. B01J 8/00
[52] U.S. Cl. .................................. 422/211; 422/236; 422/305; 435/287; 435/801
[58] Field of Search ................. 422/61, 236, 305, 306, 422/211; 435/287, 292, 293, 294, 295, 296, 299, 300, 301, 801, 810

[56] References Cited

U.S. PATENT DOCUMENTS

| 3,451,894 | 6/1969 | Anandam | 435/801 X |
| 3,616,263 | 10/1971 | Anandam | 435/287 |
| 3,773,035 | 11/1973 | Aronoff et al. | 435/295 |
| 3,913,564 | 10/1975 | Freshly | 435/295 X |
| 3,961,696 | 6/1976 | Bowie et al. | 435/801 X |
| 4,012,203 | 3/1977 | Rosiere | 422/61 X |
| 4,108,728 | 8/1978 | Spinner et al. | 435/296 |

Primary Examiner—Robert J. Warden
Attorney, Agent, or Firm—Louis E. Davidson

[57] ABSTRACT

Apparatus for generating anaerobic atmosphere is described wherein a liquid and a composition which can react with such liquid to produce a reducing gas are placed in adjacent receptacles each sealed by a rupturable film. A rupturing means can then be inserted through the rupturable films to enable the liquid and composition to come into reactive contact and generate the desired gases. A catalyst is located in an adjacent receptacle which communicates with the surrounding atmosphere to catalyze the reaction between the reducing gas and oxygen to thus remove oxygen from the surrounding atmosphere.

7 Claims, 5 Drawing Figures

GAS GENERATING APPARATUS FOR ANAEROBIC ATMOSPHERE

BACKGROUND AND DISCUSSION OF PRIOR ART

It is well-known that certain microorganisms will grow only in atmospheres that are substantially oxygen-free. Therefore, when such microorganisms are to be identified for diagnostic purposes or are to be transported or stored, it is necessary that they be maintained under anaerobic or substantially oxygen-free conditions. There are various techniques described in the prior art for obtaining such anaerobic conditions. One procedure is to evacuate the container for the microorganisms and thus eliminate any oxygen-containing atmosphere. This requires undesirable evacuation apparatus. U.S. Pat. No. 3,246,959 discloses apparatus for maintaining an anaerobic environment within a closed container. U.S. Pat. Nos. 3,616,263; 3,773,035; 3,913,564; 3,961,696; 4,012,203; 4,014,748; 4,038,148; 4,082,614 and 4,108,728 also disclose apparatus for obtaining an anaerobic environment in apparatus for storing and/or transporting microorganisms. These prior art apparatus contain oxygen-free gas, such as carbon dioxide, in pressurized containers to be released when desired or they employ compositions and catalysts to generate reducing gases which then react with oxygen to provide an oxygen-free environment or an environment wherein the oxygen content is reduced to a point where it is not harmful to the microorganisms being employed therewith. While these prior art apparatus are all capable of providing an anaerobic environment, there is still a need for a convenient apparatus for generating such anaerobic environment.

SUMMARY OF THE INVENTION

In accordance with the present invention, apparatus for generating an anaerobic atmosphere is provided which comprises in combination a first receptacle having upper and lower transversely positioned openings, a second receptacle closed at one end and having an opposite end communicating with the upper opening of said first receptacle, said second receptacle containing a liquid and having the upper opening between said second receptacle and said first receptacle sealed in a gas and liquid-tight manner with a first rupturable film, said first receptacle containing a composition capable of producing a reducing gas upon contact thereof with the liquid from said second receptacle, said first receptacle also containing an absorbent material located along and covering the first rupturable film at the upper opening thereof, said lower opening of said first receptacle being sealed in a gas and liquid-tight manner with a second rupturable film, a separate third receptacle located adjacent to said first receptacle, said third receptacle containing a catalyst capable of catalyzing the reaction between the reducing gas and oxygen, said third receptacle also having an opening enabling the catalyst to communicate with the surrounding atmosphere. This apparatus is used in conjunction with a puncturing means capable of penetrating the first and second rupturable films so as to enable the liquid in said second receptacle to pass into said first receptacle for contact with the gas-generating composition therein.

DESCRIPTION OF THE INVENTION

Figure 1:
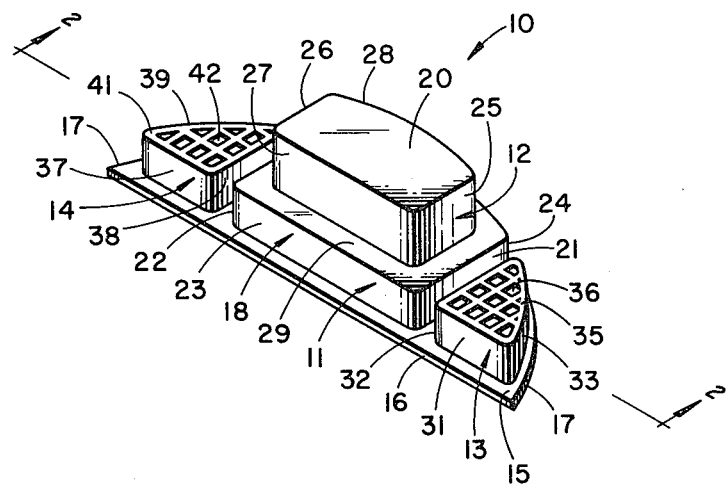
FIG. 1 is an isometric view of the apparatus of the invention.
Figure 2:
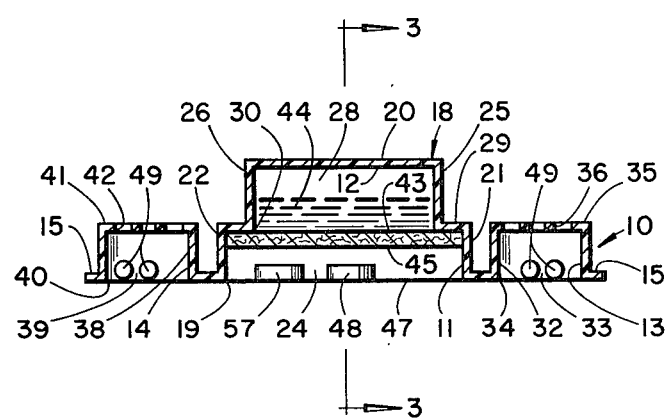
FIG. 2 is a vertical cross-sectional view of the apparatus taken along Line 2—2 of FIG. 1.
Figure 3:
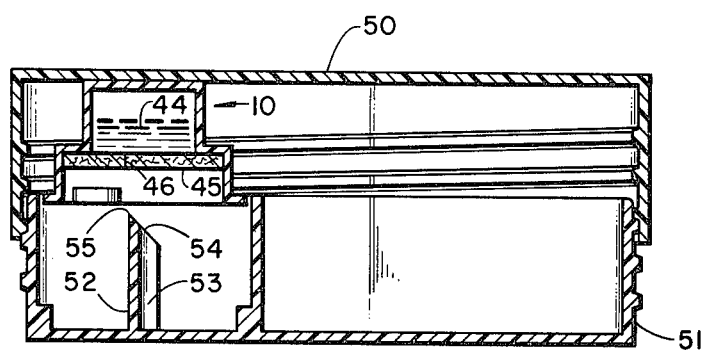
FIG. 3 is a vertical cross-sectional view of the apparatus taken along Line 3—3 of FIG. 2 but which also shows a puncturing means.

Referring to FIGS. 1 and 2, the novel apparatus of the present invention comprises a unitary molded organoplastic member 10 having first receptacle 11, second receptacle 12, third receptacle 13, fourth receptacle 14 and base 15 formed therein. As shown in FIG. 1, the base 15 has an overall crescent shape of a portion of a semi-circle with first edge 16 forming a chord and second edge 17 forming a part of a circle. Extending upwardly from base 15 is a central stepped receptacle portion 18 having an open bottom 19 and a closed upper end 20. Central receptacle 18 has a lower portion with opposing transverse side walls 21 and 22 and opposing longitudinal side walls 23 and 24 and an upper portion with opposing transverse side walls 25 and 26 and opposing longitudinal side walls 27 and 28. The side walls of the lower and upper portions of central receptacle 18 are joined through step 29 to form an opening 30 within central receptacle 18. The lower portion of central stepped receptacle portion 18 thus forms a first receptacle 11 having a lower opening 19 and an upper opening 30. The upper portion of central stepped receptacle 18 thus forms a second receptacle 12 having a closed end 20 and communicating with the upper opening 30 of first receptacle 11. The second receptacle 12 is thus supported by step 29. Third and fourth receptacles 13 and 14, respectively, extend upwardly from base 15 and are located on opposite sides of the central stepped receptacle 18. Third receptacle 13 is generally triangular in shape and has sidewalls 31, 32 and 33, an open bottom 34 and an upper end 35 with a plurality of openings 36 therein. Fourth receptacle 14 is generally triangular in shape and has sidewalls 37, 38 and 39, an open bottom 40 and an upper end 41 with a plurality of openings 42 therein. A first rupturable film 43 is attached to the step 29 in a gas and liquid-tight manner and extends across the opening 30 between the first receptacle 11 and second receptacle 12. Second receptacle 12 is filled with a liquid 44, such as water, prior to sealing of film 43 in place. A layer of absorbent material 45, such as cotton, is located along in contact with and covers the first film 43 along the upper end of first receptacle 11. As shown in FIG. 3, this absorbent layer 45 has a cut 46 through a portion thereof. A second rupturable film 47 is attached to the base 15 in a gas and liquid-tight manner and extends across the bottom openings 19, 34 and 40 of first, third and fourth receptacles, respectively. Prior to sealing film 47 in place, a reducing gas generating composition, such as pellet 48, is placed into first receptacle 11 and catalyst 49 is placed into third and fourth receptacles.

The unitary molded member 10 which forms base 15 and receptacles 11, 12, 13 and 14 is conveniently formed from an organoplastic material such as polypropylene while films 43 and 47 are conveniently formed from aluminum foil. The films are attached to the step 29 and the base 15 by any convenient means, such as adhesives. In a preferred form of the invention, the aluminum foil is coated with polypropylene. A firm bond can then be obtained between the polypropylene coating and the polypropylene molded member by heat sealing techniques.

Figure 5:
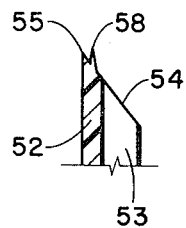
FIG. 5 is an enlarged cross-sectional view similar to that of FIG. 3 showing a preferred form of a puncturing means.
Figure 4:
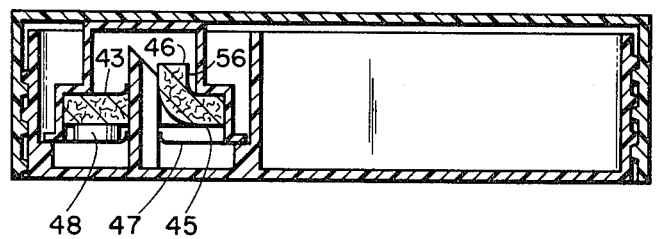
FIG. 4 is a view similar to that of FIG. 3 showing the puncturing means in an actuating position.

The above-described apparatus can be stored almost indefinitely until needed to produce an anaerobic environment. FIGS. 3 and 4 illustrate one way of using this apparatus. Member 10 is placed inside apparatus for storing or transporting a microoroganism (not shown) a portion of which apparatus has an upper member 50 threadably engaged with a lower member 51. Lower member 51 has an upwardly extending elongated member 52 located therein. Elongated member 52 has a longitudinal slot 53 located therein and an oblique end surface 54 with the trailing edge of such oblique surface communicating with slot 53. This forms a sharp leading edge 55. As members 50 and 51 are screwed together, leading edge 55 of member 52 forms a puncture means which ruptures in turn films 47 and 43 as shown in FIG. 4. In a preferred form of the puncture means shown in FIG. 5, the oblique end surface 54 has a pointed extension 58 extending therefrom. Extension 58 is located in proximity to and extends to a point coplanar with leading edge 55. The combination of leading edge 55 and extension 58 assists in rapid rupture of films 47 and 43. Absorbent layer 45 is ruptured along cut 46 and is pushed upward to form a flap 56. This flap thus moves out of the path of the cutting edge and facilitates rupture of film 43. Once film 43 is ruptured, liquid 44 an flow downward through the ruptured film and through the longitudinal slot 53 in puncture means 52. It first contacts the flap 56 and then the remainder of the absorbent layer 45 which then acts as a wick to substantially evenly distribute the liquid throughout the cross-sectional area of first receptacle 11. The absorbent layer 45 also expands as shown in FIG. 4 to come into contact with pellet 48 containing the reducing gas-generating composition.

When the reducing gas to be generated is hydrogen, the liquid 44 in second receptacle 12 is preferably water while the pellet 48 in first receptacle 11 is preferably formed from sodium borohydride. It is understood that other well-known reactions can be employed with the apparatus to generate the reducing gas. In the event that additional gases, such as carbon dioxide, are desired, additional pellets, such as pellet 57 shown in FIG. 2, are included in first receptacle 11 containing sodium carbonate and citric acid, for example. Such additional pellets (not shown in FIG. 4) will also be contacted by the expanding wet absorbent layer 45 so that water can contact them and initiate the desired gas-generating mechanism.

The reducing gas generated by the reaction in the first receptacle 11 then passes out through the rupture in film 47. The slot 53 in puncture means 52 assists in this passage. The reducing gas and oxygen in the surrounding environment can then pass through openings 36 and 42 in third receptacle 13 and fourth receptacle 14, respectively, to contact the catalyst material 49, such as palladium-coated ceramics, and initiate the chemical reaction to bind oxygen and thus remove it from the resulting anaerobic atmosphere in the space contained within members 50 and 51 and from any space within such microorganism storage or transport apparatus which communicates with the above contained space.

The above-described gas-generating apparatus can also be employed in a different manner to produce an anaerobic environment within a pouch or other container for storing or transporting microorganisms. The microorganism is placed in the pouch or other container (not shown). The above-described gas generator is placed into the pouch or other container and a puncture means is employed to rupture films 47 and 43. Any elongated member with a pointed or sharp leading edge can be forced through the films. The pouch or other container is then sealed and the desired reactions are carried out to produce the anaerobic environment.

The apparatus shown in FIG. 1 has the indicated shape so as to fit into specific microorganism transport apparatus (not shown). It is understood that the base 15 could have other shapes, such as rectangular or circular, and that the first, second, third and fourth receptacles could have other shapes. The important part of the invention is that these receptacles and related sealing films have the specific relationships described above.

What is claimed is:

1. Apparatus for generating an anaerobic atmosphere which comprises in combination a first receptacle having upper and lower transversely positioned openings, a second receptacle closed at one end and having an opposite end communicating with the upper opening of said first receptacle, said second receptacle containing a liquid and having the upper opening between said second receptacle and said first receptacle sealed in a gas and liquid-tight manner with a first rupturable film, said first receptacle containing a composition capable of producing a reducing gas upon contact thereof with the liquid from said second receptacle, said first receptacle also containing an absorbent material located along and covering the first rupturable film at the upper opening thereof, said lower opening of said first receptacle being sealed in a gas and liquid-tight manner with a second rupturable film, a separate third receptacle located adjacent to said first receptacle, said third receptacle containing a catalyst capable of catalyzing the reaction between the reducing gas and oxygen, said third receptacle also having an opening enabling the catalyst to communicate with the surrounding atmosphere.

2. Apparatus according to claim 1 wherein the first, second and third receptacles are molded from organoplastic material as a unitary structure.

3. Apparatus according to claim 1 wherein the second receptacle contains water.

4. Apparatus according to claim 1 wherein the rupturable film is aluminum foil.

5. Apparatus for generating an anaerobic atmosphere which comprises in combination the apparatus of claim 1 and a puncture means capable of penetrating said second and first rupturable films in that order so as to enable the liquid in said second receptacle to pass into said first receptacle for contact with the reducing gas-generating composition therein.

6. Apparatus according to claim 5 wherein the puncture means comprises an elongated member having a longitudinal slot therealong, said puncture means also having an end formed with an oblique surface, the leading edge of said surface forming a sharp edge and the trailing edge of said surface cmmunicating with said longitudinal slot.

7. Apparatus for generating an anaerobic atmosphere which comprises a unitary molded organoplastic article having a base, a central stepped receptacle portion having an open bottom and a closed upper end extending upwardly from said base, said central receptacle portion having a lower first receptacle having an upper opening and an upper second receptacle communicating through said upper opening with said lower first receptacle and wherein the step forms the support for said upper second receptacle, third and fourth receptacles extending upwardly from said base and being located on opposite sides of the central, stepped receptacle, said third and fourth receptacles each having an open bottom and each having a plurality of openings in the upper end thereof, said upper second receptacle containing a liquid and being sealed in a gas and liquid-tight manner with a first rupturable film which is attached to the step and extends across the upper opening of said lower first receptacle, said first receptacle containing a composition capable of producing a reducing gas upon contact with the liquid from said second receptacle, said first receptacle also containing a layer of absorbent material located along in contact with and covering said first rupturable film, said third and fourth receptacles each containing a catalyst capable of catalyzing the reaction between a reducing gas and oxygen, the open bottoms of said first, third and fourth receptacles being sealed in a gas and liquid-tight manner with a second rupturable film which is attached to the lower surface of said base and extends across said receptacle open bottoms.

* * * * *